United States Patent [19]
Oaki et al.

[11] Patent Number: 5,251,356
[45] Date of Patent: Oct. 12, 1993

[54] DEVICE FOR CLEANING PIPE PASSAGES OF MEDICAL DEVICES

[75] Inventors: Yoshinao Oaki; Hisao Yabe; Hideo Ito; Koji Koda; Akio Ogawa; Daisaku Negoro; Manabu Yajima; Yoshihiro Iida; Ichiro Nakamura; Akira Suzuki, all of Tokyo, Japan

[73] Assignee: Olympus Optical Co., Ltd., Tokyo, Japan

[21] Appl. No.: 863,410

[22] Filed: Apr. 3, 1992

[30] Foreign Application Priority Data

Apr. 12, 1991 [JP] Japan .................................. 3-080166

[51] Int. Cl.$^5$ .............................................. B08B 9/02
[52] U.S. Cl. ................... 15/104.095; 15/104.2; 15/104.33
[58] Field of Search ......... 15/104.05, 104.09, 104.095, 15/104.11, 104.2, 104.33

[56] References Cited

U.S. PATENT DOCUMENTS 4,936,312  6/1990  Tsukagoshi .

FOREIGN PATENT DOCUMENTS 374701  4/1923  Fed. Rep. of Germany ... 15/104.33

*Primary Examiner*—Edward L. Roberts
*Attorney, Agent, or Firm*—Frishauf, Holtz, Goodman & Woodward

[57] ABSTRACT

A device for cleaning pipe passages of medical devices comprises a brush having an elongated rod portion and a brush portion, a mechanism for holding and rotating the brush, a mechanism for reciprocating the brush in the pipe passage along the longitudinal axis of the brush, and a unit for controlling the rotation of the brush as well as the reciprocation of the brush in the longitudinal direction thereof.

13 Claims, 4 Drawing Sheets

DEVICE FOR CLEANING PIPE PASSAGES OF MEDICAL DEVICES

BACKGROUND OF THE INVENTION

1. Field of the Invention

The present invention relates to a device for cleaning a pipe passage such as a forceps channel in an endoscope.

2. Description of the Related Art

An endoscope is usually inserted into a cavity of a human body to check or treat some intended parts in the body cavity. The common endoscope has therein the forceps channel through which treating tools such as the forceps are introduced into the body cavity. This causes the blood and dirty matters of a patient to often enter into the forceps channel of the endoscope when some intended parts in the body cavity are checked or treated by the endoscope.

In order to protect other patients from infectious disease, therefore, the forceps channel in the endoscope which was once used for a patient and contaminated with blood and dirty matters must be cleaned.

A well-known cleaning brush is conventionally used to clean the pipe passage such as the forceps channel in the endoscope.

In order to fully clean the pipe passage in the endoscope, dirty matters stuck and hardened on the inner wall of the pipe passage, must be removed. It is however difficult to fully remove the dirty matter from the pipe passage only by use of a conventional cleaning brush. A device capable of more reliably cleaning the pipe passage than the conventional cleaning brush is accordingly required.

SUMMARY OF THE INVENTION

The object of the present invention is therefore to provide a device capable of more reliably removing dirty matter from the inner wall any of pipe passage of a medical devices.

This object of the present invention can be achieved by a device for cleaning pipe passages of medical devices comprising a brush having an elongated rod portion and a brush portion; means for holding and rotating the brush; means for reciprocating the brush in the pipe passage along the longitudinal axis of the brush; and means for controlling the movement of the brush in the longitudinal direction thereof as well as the rotation of the brush.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Figure 1:
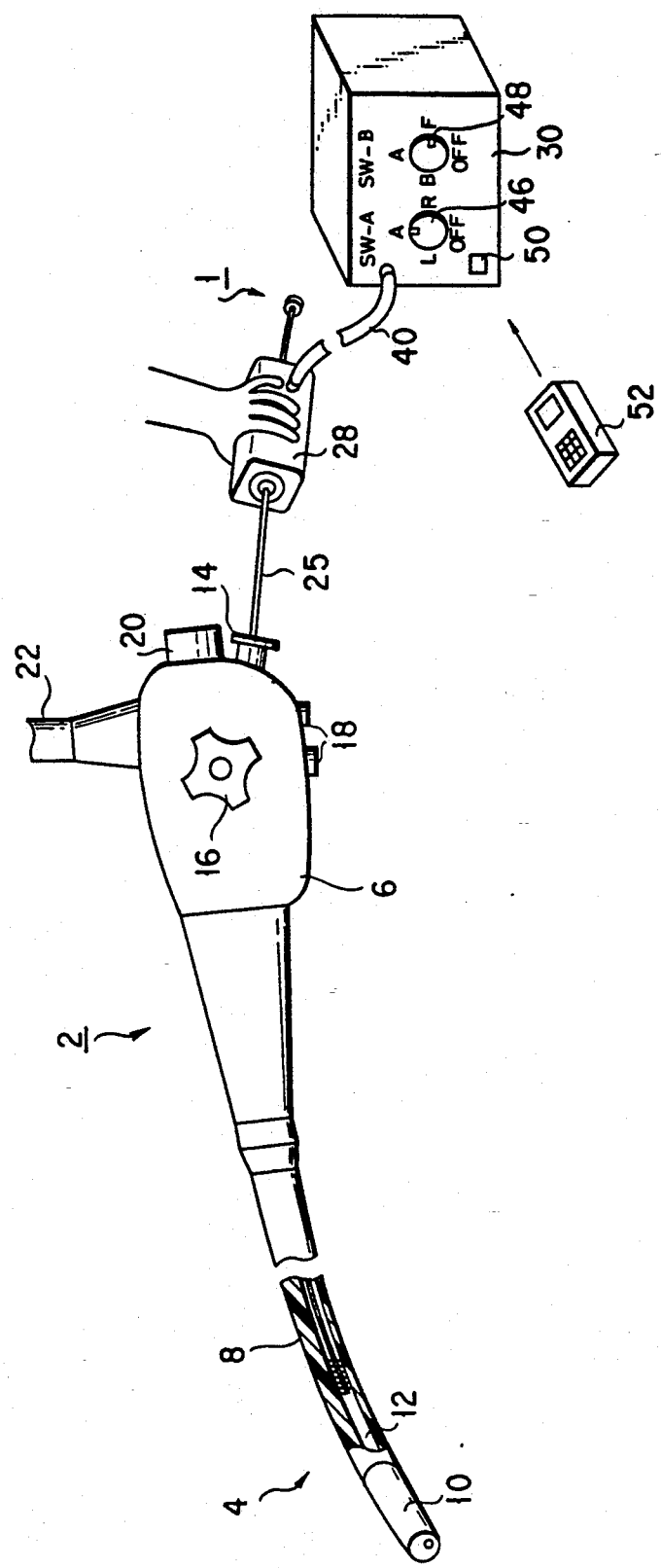
FIG. 1 is a perspective view showing the pipe passages cleaning device according to a first embodiment of the present invention.
Figure 2:
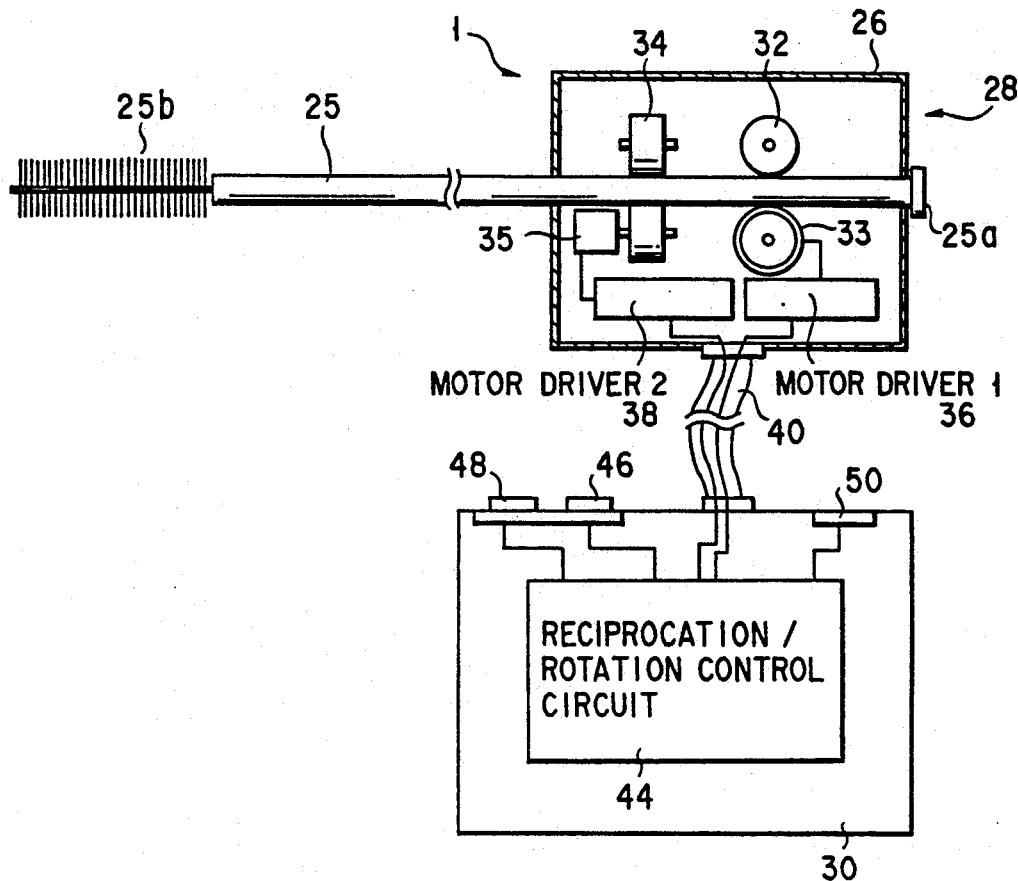
FIG. 2 shows an arrangement of the pipe passages cleaning device.
Figure 3:
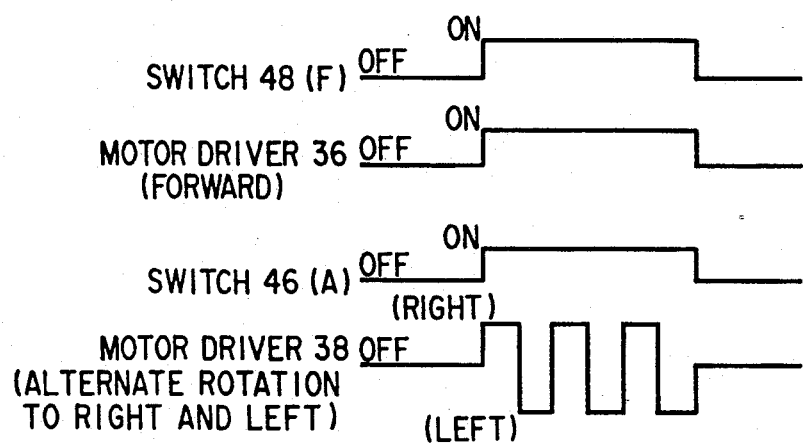
FIG. 3 is a time chart showing the operating pattern of a brush drive section.

FIGS. 1 through 3 show the pipe passage cleaning device 1 according to a first embodiment of the present invention and an endoscope 2 provided with a forceps channel 12 into which the pipe passages cleaning device 1 is inserted.

The endoscope 2 includes an inserting section 4 adapted to be inserted into a cavity of a human body, and an operating section 6. The inserting section 4 includes flexible and curving pipe portions 8 and 10. The inserting section 4 has therein the forceps channel 12 into which treating tools such as the forceps can be inserted, and the forceps channel 12 has a tools inlet 14 at the rear end thereof.

The operating section 6 connected to the rear end of the inserting section 4 includes an angle knob 16 for curve-operating the curving portion 10, and air and water supply buttons 18. The operating section 6 also has an observation eyepiece 20 at the rear end thereof. A universal cord 22 is connected to the operating section 6 and the other front end of the universal cord 22 is connected to an air and water supply and a light source units (not shown). The forceps channel 12 is opened at the front end face of the inserting section 4.

The pipe passage cleaning device 1 has a system for automatically reciprocating and rotating an endoscope cleaning brush.

As shown in FIG. 1, the pipe passage cleaning device 1 comprises mainly the long brush 25, a brush drive section 28 and a control section 30.

As shown in FIG. 2, the brush drive section 28 has a case 26 in which a pair of reciprocating rollers 32 and a pair of rotating rollers 34 are freely rotatably housed. The brush 25 is held between the reciprocating rollers 32 and between the rotating rollers 34. A first motor 33 is connected to the reciprocating rollers 32 to rotate them in a direction in which the brush 25 is reciprocated. A first motor driver 36 is connected to the first motor 33. On the other hand, a second motor 35 is connected to the rotating rollers 34 to rotate them in a direction in which the brush 25 is rotated. A second motor driver 38 is connected to the second motor 35.

The brush 25 has an elongated rod portion and a stopper 25a formed at the rear end thereof, and this, stopper 25a serves to limit the forward movement of the brush 25 and to prevent the brush 25 from coming out of the case 26 or brush drive section 28. The brush 25 also has a filaments-planted brush portion 25b at the front end thereof.

The brush drive section 28 is connected to the control section 30 via cords 40. The control section 30 has a reciprocation/rotation control circuit 44, to which the first and second motor drives 36, 38, a first rotation switch 46 (SW-A), a second reciprocation switch 48 (SW-B) and a remote control light receiving device 50 are electrically connected. The operating mode of the brush 25 can be switched between a full rotation to right (R) or left (L) and an alternate minute rotation (A) to right and left by the first switch 46. It can also be switched between a full movement to forward (F) or backward (B) and an alternate minute movement (A) to forward and backward by the second switch 48.

The control section 30 can be made operative by a remote control switch 52 shown in FIG. 1. When the remote control switch 52 is turned on, therefore, infrared rays shot from the remote control switch 52 are received by the remote control light receiving device 50 and a signal is sent to the reciprocation/rotation control circuit 44 to control the brush drive section 28.

When the switch 48 is switched forward (F) as shown in FIG. 3, for example, signal is sent to the first motor driver 36. The first motor 33 is thus driven to rotate the rollers 32 so as to move the brush forward. When the switch 46 is switched to the alternate minute rotation mode (A) at the same time, a signal is sent to the second motor driver 38, by which the second motor is driven to rotate the rollers 34 so as to rotate the brush 25 minutely and alternately to the right and left. When the brush 25 is inserted into the forceps channel 12 through the tools inlet 14 of the endoscope 2 while keeping the brush 25 under the above-described state, the forceps channel 12 can be automatically cleaned by the brush 25.

The reciprocation and rotation of the brush 25 can be made to occur at the same time or independently of the other.

The brush 25 may be rotated in one direction at high speed instead of its being rotated minutely and alternately to the right and left. Further, it can be reciprocated at a high speed of about 10 cm/sec. as well as at low speed.

When the operator inserts the front end of the brush 25 into the channel 12 through the tools inlet 14, the subsequent cleaning operation of the brush 25 can be made automatic in the case of the above-described pipe passages cleaning device. The operator, this, time, may only grasp the brush drive section 28 with one hand. When he grasps the brush drive section 28 with one hand, he can operate the remote control switch 52 with the other hand.

The pipe passages cleaning device enables pipe passages of medical devices to be more easily cleaned without soiling the clothes of the operator with dirty matters in the pipe passages. In addition, that portion of pipe passages where two pipe are coupled to each other can be more easily cleaned by the reciprocating rotation of the brush 25.

Figure 4:
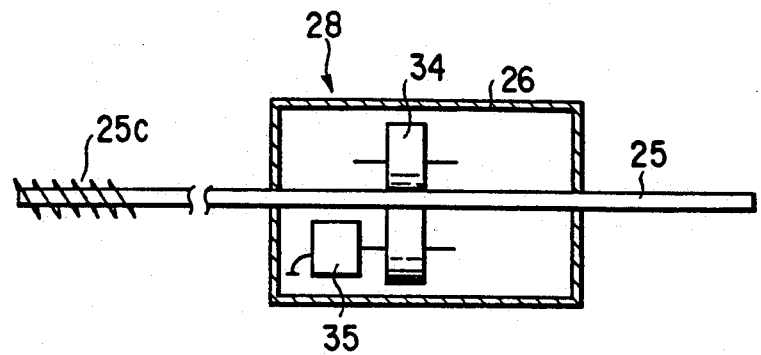
FIG. 4 is a partly-sectioned side view showing the pipe passages cleaning device according to a second embodiment of the present invention.

FIG. 4 shows only a brush and a brush drive section of the pipe passages cleaning device according to a second embodiment of the present invention. No control section is shown in FIG. 4 but it is the same in structure as the one in the first pipe passages cleaning device.

As shown in FIG. 4, the brush 25 is passed through the case 26 of the brush drive section 28 and held between a pair of the rotation rollers 34 in the case 26. The motor 35 is connected to the rotation rollers 34 and it is further connected to the motor driver at the control section (not shown). The brush 25 has a brush portion 25c where filaments are planted in a spiral shaped pattern.

When the brush 25 is rotated in the forceps channel 12 of the endoscope 2, its brush portion 25c is reciprocated like a drill in the forceps channel 12 because the filaments at the brush portion 25c are planted in a spiral. Even when the brush drive section 28 has no means which serve to reciprocate the, brush 25, the brush 25 only rotates and can be reciprocated in the pipe passage of the endoscope by a manual operation.

Figure 5:
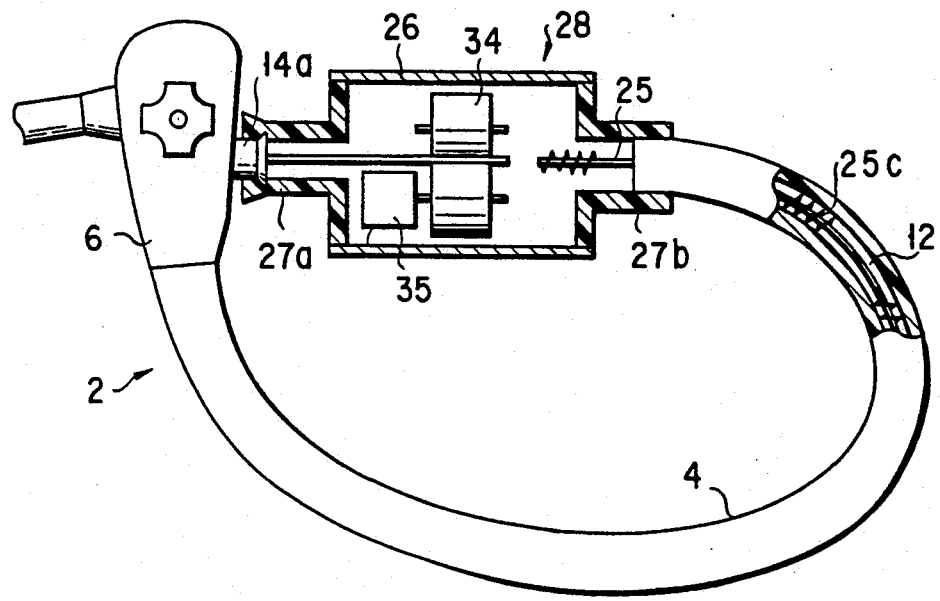
FIG. 5 shows a modification of the second pipe passages cleaning device.
Figure 6:
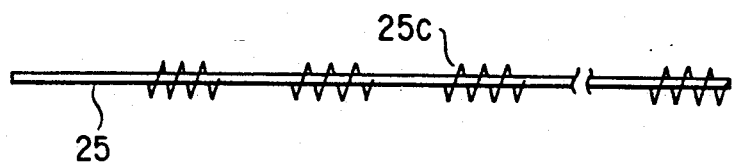
FIG. 6 is a side view showing the brush in FIG. 5.

FIG. 5 shows a modification of the second pipe passages cleaning device.

This modification has the same brush drive section 28 as that in the second pipe passages cleaning device, but a brush inserting projection 27a is projected from the front face of the case 26 while a brush receiving projection 27b to which a tools inlet of the endoscope can be connected is projected from the rear face of the case 26. In addition, the brush 25 includes plural brush portions 25c separated by a certain distance in the longitudinal direction of the brush 25. Filaments at each brush portion 25c are planted in a spiral. The brush 25 is held between the paired rollers 34 but it can be freely released from them.

The brush inserting projection 27a of the case 26 is fitted onto the tools inlet 14a of the operating section 6 and the front end of the inserting section 4 is fitted into the brush receiving projection 27b of the case 26 while curving the inserting section 4 of the endoscope 2. When the motor is driven in this state to rotate the brush 25 with the rollers 34, the brush 25 is moved forward in the forceps channel 12 because the filaments at each brush portion 25c are planted in a spiral shaped pattern. The brush 25 is then projected through the open front end of the forceps channel 12 in the inserting section 4 and again entered into the brush drive section in the case 26. As the brush 25 advances, its front end is held between the paired rollers 34 and is again inserted into the forceps channel 12. The rear and front ends of the brush 25 are temporarily held between the rollers 34 in this case.

According to this modification, the forceps channel in the endoscope can be continuously cleaned even when the brush drive section 28 has no means which serves to reciprocate the brush.

Although the brush has been moved forward into the pipe passage by the reciprocation rollers and by the spiral brush portion(s) in the above cases, it may be moved forward by the pressure of water which is supplied from the brush drive section into the pipe passage in the endoscope by the water supply system. It can be moved backward in this case by the spiral brush portion(s).

Figure 7:
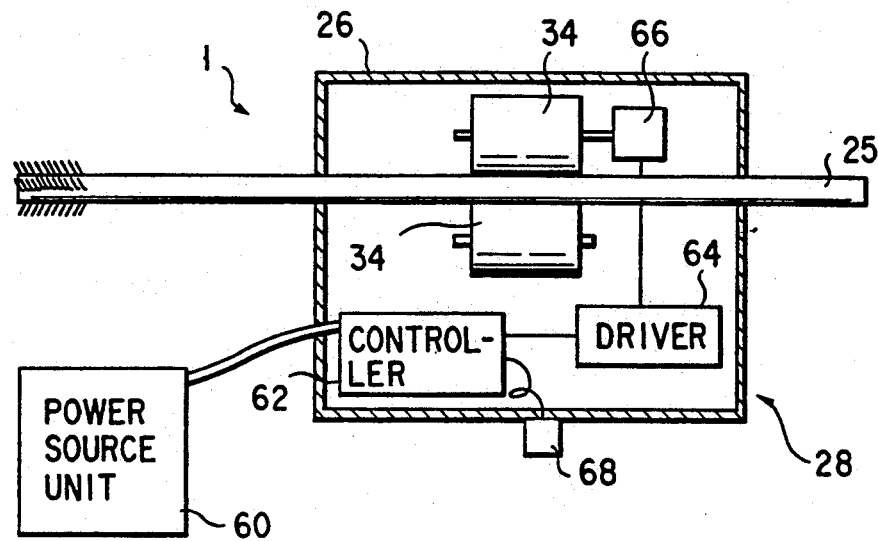
FIG. 7 partly shows a modification of the brush drive section in the pipe passages cleaning device.

FIG. 7 shows modifications of the brush drive section and the control section in the second pipe passages cleaning device.

This pipe passages cleaning device 1 comprises a brush drive section 28 and a power source unit 60. The brush drive section 28 includes a controller 62, a motor driver 64, a motor 66 and a pair of rollers 34. The case 26 in which the brush drive section 28 is arranged has a control switch 68. The brush drive section 28 and the power source unit 60 may be made as one unit.

According to this pipe passages cleaning device, a signal is sent to the driver 64 via the controller 62 when the control switch 68 is switched on. The motor 66 is thus driven. The controller 62 has a CPU (not shown)

and it is programmed to change the reciprocating speed and amplitude of the brush. The whole of the pipe passages cleaning device can be smaller-sized in this case.

Figure 8:
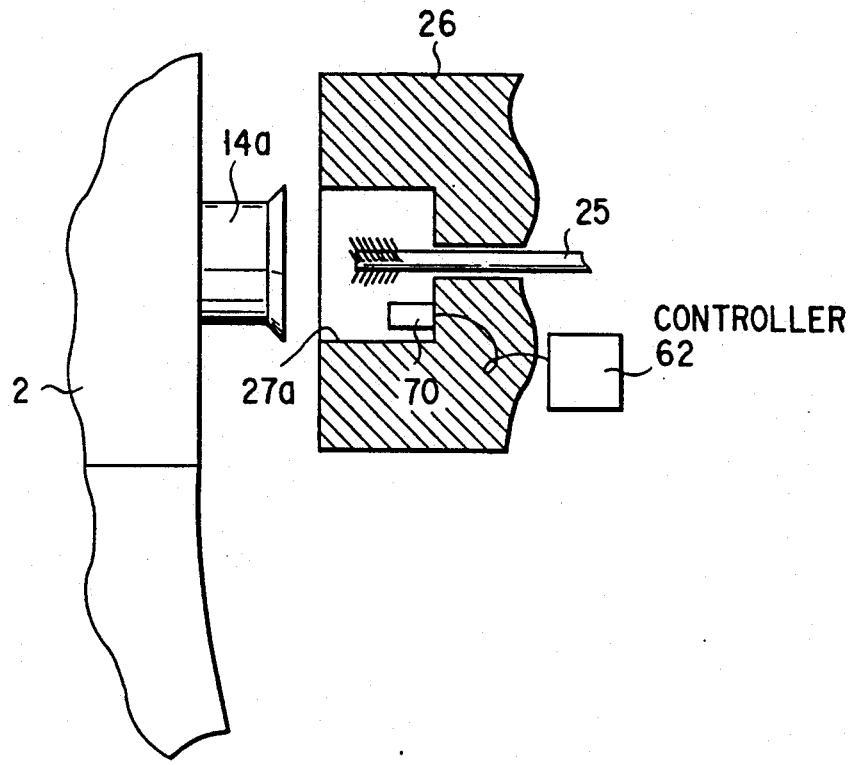
FIG. 8 partly shows another modification of the brush drive section in the pipe passages cleaning device.

FIG. 8 shows a modification of the brush drive section in FIG. 5. The brush inserting projection 27a of the brush drive section 28 shown in FIG. 5 has a sensor 70 which can detect that the brush inserting projection 27a is fitted onto the tools inlet 14a of the endoscope 2. The sensor 70 is an ON/OFF switch, for example, and when this switch 70 is put ON, the brush drive section 28 is made operative by the controller 62. The pipe passages cleaning device can be made operative in this case immediately after the brush drive section 28 is attached to the endoscope 2.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A device for cleaning a pipe passage of an endoscope comprising:
   a brush having an elongated rod portion and a brush portion;
   a case for supporting the elongated rod portion;
   rotating means, including a first motor and a first motor driver electrically connected to the first motor, for rotating the brush;
   moving means, including a second motor and a second motor driver electrically connected to the second motor, for moving the brush in a longitudinal direction of the elongated rod portion of the brush; and
   control means for controlling the first and second motor drivers, such that the rotating means rotates the brush independent of the moving of the brush by the moving means.

2. The pipe passages cleaning device according to claim 1, wherein said brush portion includes plural brush parts separated from one another by a certain distance along the elongated rod portion thereof.

3. The pipe passages cleaning device according to claim 1, wherein said rotating means includes a pair of first rollers that are in contact with the rod portion of the brush, the first motor being connected to one of the first rollers, and the first motor driver being electrically connected to the first motor, said rotating means being housed in said case.

4. The pipe passages cleaning device according to claim 3, wherein said control means has a control switch attached to the case housing said rotating means.

5. The pipe passages cleaning device according to claim 3, wherein said case also houses said moving means, said moving means including a pair of second rollers in contact to the rod portion of said brush, said second motor being connected to one of the pair of second rollers, and the second motor driver being electrically connected to the second motor.

6. The pipe passages cleaning device according to claim 1, wherein said rotating means further includes a brush inserting projection that is adapted to fit into a tool inlet of an endoscope, and a brush receiving projection adapted to fit onto a front end of an inserting section of the endoscope.

7. The pipe passages cleaning device according to claim 6, wherein said rotating means has rollers, and said brush is clamped between the rollers so as to move along the longitudinal axis thereof when released from the rollers.

8. The pipe passages cleaning device according to claim 1, wherein said rotating means further includes a brush inserting recess adapted to fit onto a channel inlet of an endoscope, and a sensor arranged in a brush inserting recess for detecting that said rotating means is connected to the channel inlet of the endoscope.

9. The pipe passages cleaning device according to claim 1, wherein said control means includes means for changing an operating mode of the brush between one of a full speed rotation in a righthand direction, a full speed rotation in a lefthand direction, a less than full speed rotation in said righthand direction and a less than full rotation in said lefthand direction.

10. A device for cleaning a pipe passage of an endoscope, comprising:
    a brush including an elongated cylindrical shaped rod portion and a brush portion having filaments thereon which are arranged in a spiral along the brush portion;
    said brush being movable in an axial direction of the elongated rod portion when the brush is rotated while the brush portion of the brush is in contact with an inner wall of the pipe passage;
    a case for supporting the elongated rod portion of the brush such that said elongated rod portion is longitudinally movable relative to the case;
    rotating means, including a motor and a motor driver electrically connected to the motor, for rotating the brush so that the rotation of the brush moves the brush in the axial direction of the elongated cylindrical rod when the brush portion is in contact with the pipe passage of the endoscope; and
    control means for controlling the motor driver.

11. A device for cleaning a pipe passage of an endoscope, comprising:
    a brush including an elongated shaft portion and a brush portion;
    a case for supporting the elongated shaft portion of the brush;
    rotating means, including a motor and a motor driver electrically connected to the motor, for rotating the brush; and
    a fitting portion for enabling the case to be detachably attached to one of a channel inlet of the endoscope, the fitting portion being provided at an open portion of the case, the brush extending through the open portion of the case.

12. A device for cleaning pipe passages of medical devices comprising:
    a brush having an elongated rod portion and a brush portion;
    rotation means for holding and rotating the brush;
    reciprocation means for reciprocating the brush in the pipe passage along a longitudinal axis of the brush;
    control means for controlling a movement of the brush along the longitudinal axis thereof and for controlling the rotating of the brush by the rotation means;
    said rotation means including a case for housing a pair of first rollers that are in contact with the rod portion of the brush, a first motor connected to one of the rollers, and a first motor driver electrically connected to the first motor; and said case further housing said reciprocation means, said reciprocation means including a pair of second rollers in contact with the rod portion of said brush, a second motor connected to one of the second rollers, and a second motor driver electrically connected to the second motor.

13. A device for cleaning pipe passages of medical devices comprising:

a brush having an elongated rod portion and a brush portion; rotation means for holding and rotating the brush;

reciprocation means for reciprocating the brush in the pipe passage along a longitudinal axis of the brush;

control means for controlling a movement of the brush along the longitudinal axis thereof and for controlling the rotating of the brush by said rotation means; and said control means including means for changing an operating mode of the brush between one of a full speed rotation in a righthand direction, a full speed rotation in a lefthand direction, a less than full speed rotation in the righthand direction and a less than full speed rotation in the lefthand direction.

* * * * *